(12) United States Patent
Karlsson et al.

(10) Patent No.: US 7,390,373 B2
(45) Date of Patent: Jun. 24, 2008

(54) METHOD FOR PRODUCTION OF DIAPER PANTS HAVING A DETACHABLE AND RESEALABLE CONNECTION MEMBER

(75) Inventors: Birgitta Karlsson, Mölndal (SE); Johan Skogsberg, Göteborg (SE); Lennart Erwast, Göteborg (SE); Urban Widlund, Pixbo (SE); Ingemark Fernfors, Mölndal (SE)

(73) Assignee: SCA Hygiene Products AB, Gothenburg (SE)

( * ) Notice: Subject to any disclaimer, the term of this patent is extended or adjusted under 35 U.S.C. 154(b) by 209 days.

(21) Appl. No.: 11/317,094

(22) Filed: Dec. 27, 2005

(65) Prior Publication Data

US 2006/0135928 A1 Jun. 22, 2006

Related U.S. Application Data

(63) Continuation of application No. 10/401,688, filed on Mar. 31, 2003, now abandoned.

(60) Provisional application No. 60/368,964, filed on Apr. 2, 2002.

(51) Int. Cl.
*A61F 13/15* (2006.01)
(52) U.S. Cl. .................... 156/204; 156/226; 156/227
(58) Field of Classification Search ................ 156/202, 156/204, 226, 227
See application file for complete search history.

(56) References Cited

U.S. PATENT DOCUMENTS 5,685,873 A 11/1997 Bruemmer
5,830,206 A 11/1998 Larsson
6,022,432 A 2/2000 Elsberg et al.

(Continued)

FOREIGN PATENT DOCUMENTS

DE 94 22 298 U1 12/1999

(Continued)

OTHER PUBLICATIONS

Letter from a Columbian patent agent which indicates the degree of relevance of WO 01/87210 A1 found by the foreign office, Dec. 3, 2007.

(Continued)

*Primary Examiner*—Richard Crispino
*Assistant Examiner*—Barbara J. Musser
(74) *Attorney, Agent, or Firm*—Buchanan Ingersoll & Rooney PC

(57) ABSTRACT

Method for producing disposable diaper-pants having openable and resealable side panels. Absorption bodies are applied on a continuous web of inner or outer coversheet material so that front portions and rear portions of adjacent diaper-pants blanks in a web are directed toward each other. A continuous web of outer or inner coversheet material is applied to and secured to the web with absorption bodies. Separate side panels connected to each other by a detachable and resealable connection are secured to side portions of the adjacent front portions or rear portions of the diaper pants. Each diaper-pants blank with side panels is cut from the web and folded about a transverse axis in the crotch with the front and rear edges lying against each other. The side panels of each blank are folded toward and secured to side portions of the rear or front portion which have no side panel.

6 Claims, 3 Drawing Sheets

U.S. PATENT DOCUMENTS

| | | | |
|---|---|---|---|
| 6,036,805 | A | 3/2000 | McNichols |
| 6,113,717 | A | 9/2000 | Vogt et al. |
| 6,238,725 | B1 | 5/2001 | Bush et al. |
| 6,287,287 | B1 | 9/2001 | Elsberg |
| 6,447,497 | B1 | 9/2002 | Olson |
| 6,508,797 | B1 | 1/2003 | Pozniak et al. |
| 6,783,487 | B2 | 8/2004 | Duhm et al. |
| 6,846,374 | B2 * | 1/2005 | Popp et al. .................. 156/85 |
| 2004/0044325 | A1 | 3/2004 | Corneliusson |

FOREIGN PATENT DOCUMENTS

| | | |
|---|---|---|
| SE | 508613 C2 | 1/1999 |
| WO | 95/27461 | 10/1995 |
| WO | 99/65438 A1 | 12/1999 |
| WO | 99/65439 A1 | 12/1999 |
| WO | 99/65441 A1 | 12/1999 |
| WO | 00/37007 A1 | 6/2000 |
| WO | 00/37010 A1 | 6/2000 |
| WO | WO 01/87210 A1 | 11/2001 |

OTHER PUBLICATIONS

PCT International Search Report, PCT/SE03/00491, dated Jun. 2, 2003.

* cited by examiner

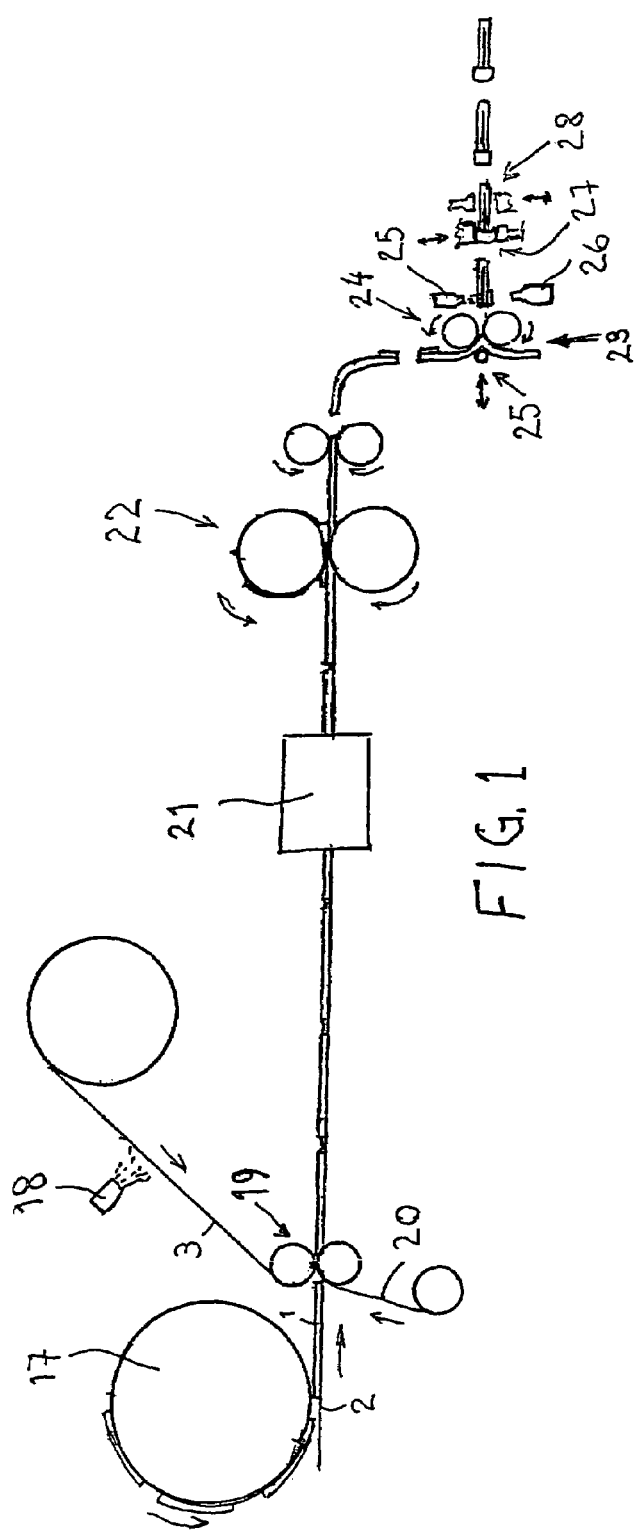
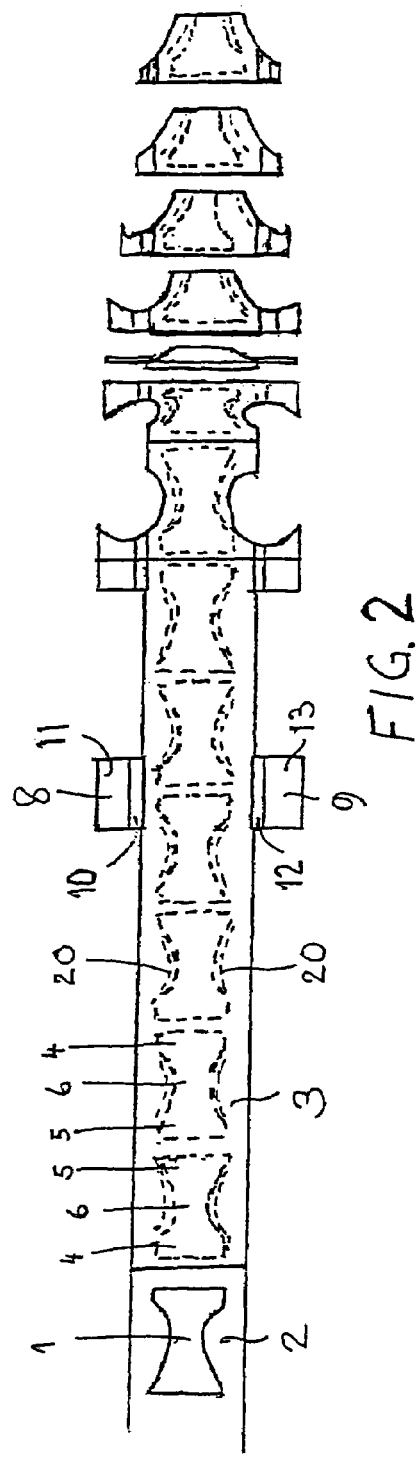

METHOD FOR PRODUCTION OF DIAPER PANTS HAVING A DETACHABLE AND RESEALABLE CONNECTION MEMBER

CROSS-REFERENCE TO RELATED APPLICATIONS

This application is a continuation application of Application No. 10/401,688, filed Mar. 31, 2003, now abandoned entitled METHOD FOR PRODUCTION OF DIAPER PANTS, which is incorporated herein by reference. The present application claims the benefit of U.S. Provisional Application No. 60/368,964, filed in the United States on Apr. 2, 2002, the entire contents of which are hereby incorporated herein by reference.

BACKGROUND OF THE APPLICATION

1. Technical Field

The present invention relates to a method for production of disposable diaper pants or of a sanitary panty of the disposable type with openable and resealable side panels, and to diaper pants or a sanitary panty produced by means of this method.

2. Background Art

Diaper pants with openable and resealable side panels combine the advantages of conventional diaper pants and conventional diapers. They are produced with sealed side panels and, like conventional diaper pants, can be taken off and put on in the same way as underpants. By means of the side panels being openable, they can also be taken off in the same way as conventional diapers, as a result of which they can be changed without underpants, shoes and stockings having to be taken off, and soiling of the infant can be avoided when changing the diaper pants. Moreover, the fact that they are resealable means that a parent can open the diaper pants in order to check whether they need to be changed and can seal the diaper pants again if this is not the case. It is therefore of advantage to be able to produce such diaper pants in an economic way.

SE-C2-508 613 discloses a method for producing diaper pants from a web of continuous diaper pants blanks, in which the blanks are arranged side by side. In this method, the whole web of diaper pants blanks is folded so that front edges and rear edges lie edge-to-edge, and the side portions of the folded diaper pants blanks are secured to each other with the aid of a folded band. The folded band can be in two parts, said two parts being connected to each other by means of a detachable and resealable connection. The band does not normally form separate side panels, but it is stated that bands folded in a bellows fashion can be used if it is desired to use parts of the bands to form side panels. Such folding in a bellows fashion complicates the method and requires great precision when applying the bellows-folded bands. The document also mentions that, in the case of a web of continuous diaper pants blanks in which the diaper pants blanks are arranged one after another, it is possible to connect the side portions of individual diaper pants blanks to each other with the aid of folded bands. Such a method requires great precision both when applying the bands and when cutting the individual diaper pants blanks from the web of continuous diaper pants blanks.

WO 99/65439, WO 99/65441, WO 00/37007 and WO 00/37010 all disclose methods for producing diaper pants in which side panels are fastened in a detachable and resealable manner to side portions of the unit of the diaper pants which encloses the absorption body. These methods too require great precision when applying the side panels and when cutting the individual diaper pants blanks from the web of continuous diaper pants blanks. These methods also make it difficult to design the openable and resealable connection as a childproof connection.

It is an object of the present invention to make available a method for production of disposable diaper pants or of a sanitary panty of the disposable type with openable and resealable side panels, said method requiring less precision than in previously known methods when applying side panels to a web of continuous diaper pants blanks arranged in succession, and when subsequently cutting individual diaper pants blanks from the web. A further object is to permit application of childproof connections in a simple manner.

SUMMARY OF THE INVENTION

These and other objects are achieved by means of a method for production of disposable diaper pants or of a sanitary panty of the disposable type with openable and resealable side panels.

A web of interconnected diaper pants blanks, which each comprise an absorption body enclosed between an inner cover sheet of liquid-permeable material and an outer cover sheet of liquid-impermeable material and have a front portion and a rear portion and an intermediate crotch portion, is formed by applying a row of absorption bodies on a continuous web of inner or outer cover sheet material so that the front portions and the rear portions of adjacent diaper pants blanks in the web of interconnected diaper pants blanks are directed toward each other, after which a continuous web of outer or inner cover sheet material is applied to the web with absorption bodies and secured to it in those parts thereof which lie outside the absorption bodies.

Separate side panels connected to each other are secured to the side portions of each of the adjacent front portions or each of the adjacent rear portions of the diaper pants blanks, each side panel comprising two parts which are connected to each other by means of a detachable and resealable connection. Individual diaper pants blanks provided with side panels are cut out from the web of interconnected diaper pants blanks. Each diaper pants blank is folded about a transverse axis in the crotch portion so that the front and rear edges of the blank lie against each other. Thereafter the side panels of each diaper pants blank are folded in toward those side portions of either the rear portion or front portion which have no side panel and are secured thereto.

Because the diaper pants blanks are arranged so that the front portion of one blank adjoins the front portion of the preceding or subsequent blank and the rear portion of one blank adjoins the rear portion of the subsequent or preceding blank, the blanks can have the same width at the locations for division. This means that the precision requirements for division are reduced compared to the situation where parts with different widths are to be divided. The precision requirements for application of side panels are also reduced. Moreover, the application of two-part side panels means that the connection between the two parts can be made childproof before the application of the side panels to the web of diaper pants blanks.

In a preferred embodiment, the side panels are secured to the outer or inner cover sheet of the diaper pants blanks. Alternatively, the side panels are placed between the outer and inner cover sheets of the web of connected diaper pants blanks and are secured to both of these sheets. The side panels preferably comprise at least partially an elastic material, and the detachable and resealable connection, which connects the two parts of each side panel to each other, comprises a childproof connection. In one variant, in addition to the detachable and resealable connection, each side panel also comprises a second childproof detachable connection, which is destroyed when the side panel is opened for the first time.

Embodiments of the invention also relate to disposable diaper pants or a sanitary panty of the disposable type with a front portion, a rear portion and an intermediate crotch portion, which comprises an absorption body enclosed between an inner cover sheet of liquid-permeable material and an outer cover sheet of liquid-tight material and separate side panels which, on both sides of the absorption body, extend outside the inner and outer cover sheets and connect the front and rear portions of the diaper pants to each other, so that the diaper pants acquire a pants-like configuration with a waist opening and two leg openings. Each side panel is elastic and comprises two parts which are connected to each other by means of a detachable and resealable connection member.

In a preferred embodiment, the detachable and resealable connection comprises a childproof connection member, and the elastic side panels include parts of nonelastic material in those sections to which parts of the connection members are secured. In one variant, in addition to the detachable and resealable connection, each side panel comprises a second childproof detachable connection, which is destroyed upon opening the side panel for the first time. The force needed to open the childproof connection is greater than 4 N, preferably greater than 6 N, more preferably 8 N, and most preferably 10 N but less than 20 N, preferably about 15 N.

BRIEF DESCRIPTION OF THE DRAWINGS

The invention will now be described with reference to the attached figures, of which:

FIGS. 1 and 2 are diagrammatic representations, in a side view and plan view respectively, of an arrangement for producing diaper pants according to a first embodiment of the invention.

DETAILED DESCRIPTION OF THE PREFERRED EMBODIMENTS

Figure 3:
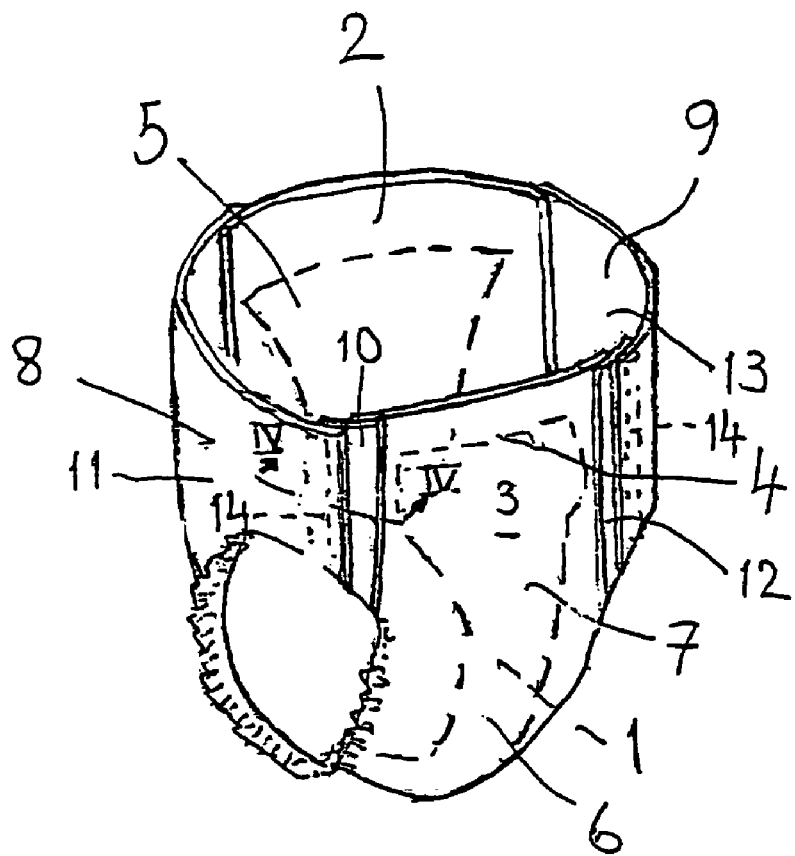
FIG. 3 shows a diagrammatic perspective view of diaper pants produced in an arrangement according to FIGS. 1 and 2.

FIGS. 1 and 2 are diagrammatic representations of an arrangement for producing the diaper pants according to FIG. 3. The diaper pants shown in FIG. 3 comprise an absorption body 1 enclosed between an inner cover sheet 2 of liquid-permeable material and an outer cover sheet 3 of liquid-tight material. The cover sheets 2 and 3 are connected to each other by adhesive bonding or welding in parts lying outside the absorption body. The unit 7 formed by the cover sheets and the absorption body has a front portion 4, a rear portion 5 and an intermediate narrower crotch portion 6. The diaper pants 3 also comprise side panels 8, 9 which extend between the front and rear portions of the unit 7 lying on the same sides of the absorption body and connect these portions to each other so that the diaper pants acquire a form similar to underpants.

Figure 5:
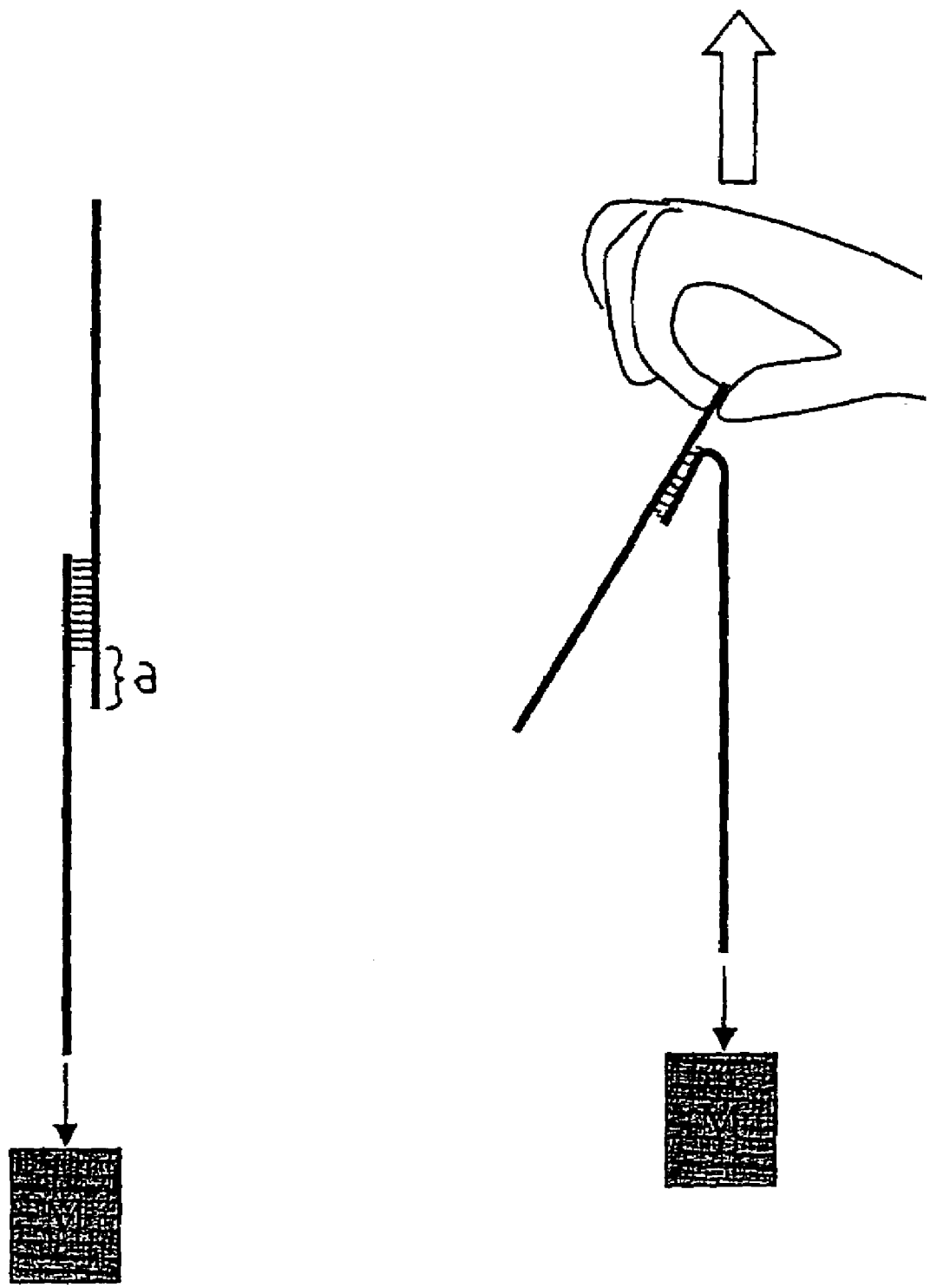
FIG. 5 is a diagrammatic representation of a method for testing the childproof nature of a connection.

The side panels 8, 9 comprise two parts 10, 11 and 12, 13, respectively, which parts overlap each other and are connected to each other by means of a detachable and resealable mechanical connection 14 in the overlapping portions. In the example shown, the connection 14 is or is similar to a VELCRO™ type connection, i.e., one part 10 is provided with a fastening element 15, or male element, having a number of hooks which project outward from the surface of the fastening element, and the other part 11 is provided with a fastening element 16, or female element, having a number of loops or eyelets in which the hooks engage. In the illustrative embodiment shown, some of the hooks of the male element are also firmly connected to the female element, e.g. firmly welded in the female element by point welding. In this way it is possible to obtain a connection which is difficult or impossible for an infant to open but is easy for an adult to open. It has indeed been found that infants like to manipulate their diaper pants, and for this reason there is a need for a childproof connection. The number of weld points should be chosen so that the force needed to open such a connection is greater than 4 N, preferably greater than 6 N, more preferably greater than 8 N, and most preferably greater than 10 N but less than 20 N, preferably less than 15 N, in order to ensure childproofing and yet make the connection easy for an adult to open. The opening force can be easily measured, in the manner shown diagrammatically in FIG. 5, by coupling a weight to that part of the two parts of the connection which is overlapped, and thereafter taking hold of the grip part of the overlapping part and then lifting the connection. If the weight remains suspended from the connection for more than 30 seconds without the connection opening, the connection is considered sufficient to hold the weight.

Another factor which influences the childproof aspect is the length of the grip tab, i.e. the length a (see FIG. 5) of that part of the overlapping side panel which projects beyond the connection. It has been found that if the grip tabs are shorter than 7 mm, it is very difficult for the children themselves to open the connection. For this reason, the length of the grip tab should lie between 3 and 7 mm, preferably between 4 and 6 mm.

The childproofing can also be obtained in another way by means of the fact that, outside the mechanical connection 14, the overlapping portions of the two parts 10, 11 and 12, 13, respectively, of the side panels are connected to each other by means of a second openable but not resealable connection, for example a weld connection or adhesive connection, with an opening force in accordance with the above. A second connection of this kind is destroyed when the side panels are opened for the first time. The outermost edge part of the overlapping part of the two parts 10, 11 and 12, 13, respectively, can also be firmly connected to the underlying part of the side panel, in which case opening is obtained by means of a line of weakening in the overlapping part situated between the connection 14 and the firmly connected outermost edge part.

The two-part side panels 8, 9 can be elastic and are preferably made of elastic material, except in those parts which include the securing elements 15, 16, which parts are preferably made of nonelastic material. The elastic material can include, for example, elastics made from block copolymers, such as polyurethanes, copolyether esters, polyamide-polyether block copolymers, ethylene-vinyl acetates (EVA) and the like, including polyurethanes available from E. I. Du Pont de Nemours Co., USA, under the name LYCRA® (also known as "spandex"); elastomeric styrene-butadiene copolymers, including those such as KRATON® material, which are available from Shell Chemical Company of Houston, Tex., USA; tetra-block copolymers, including elastomeric styrene-poly(ethylenepropylene) block copolymers available from Shell Chemical Company of Houston, Tex., USA, under the trade name KRATON®; polyamides including polyether block amides available from Ato Chemical Company, USA, under the trade name PEBAX®; polyesters, such as those available from E. I. Du Pont de Nemours Co. under the trade name HYTREL®; single-site or metallocene-catalyzed polymers, including single-site or metallocene-catalyzed polyolefins with a density of less than about 0.89 gram/cm$^3$ from Dow Chemical Co., USA, under the trade name AFFINITY®; and natural and synthetic rubber. The nonelastic material can be, for example, a nonwoven material, for example a spunbond nonwoven, a carded nonwoven, a meltblown nonwoven or a nonwoven laminate, for example a spunbond-meltblown-spunbond (SMS) laminate. The fibers used to build up the nonwoven materials can be fibers of polyolefins, for example polyethylene or polypropylene, or of polyester. Moreover, the nonwoven material can be a mixture of several different types of fibers, or of fibers which has several different polymers, called copolymers. It is also possible for the nonelastic material to be a plastic film. In the preferred embodiment, therefore, at least the parts 11 and 13 of the two 10, 11 and 12, 13, respectively, of which the side panels 8, 9 consist, are in turn made up of at least two parts. For the sake of simplicity, however, the parts 10, 11 and 12, 13, respectively, are shown as single material pieces in the figures.

The aim of the elastic side panels is to give the diaper pants a good fit. The side panels are dimensioned to give the elastic force necessary, but not more. It is therefore conceivable that the side panels also have parts of nonelastic material at locations other than at the securing elements.

As material for the side panels, it is also conceivable to use two nonwoven sheets between which elastic material, elastic bands or elastic threads are secured in the stretched state. With such a material, the elastic and nonelastic parts of the side panels include portions with and without such elastic material.

To improve access to the detachable and resealable connections 14, the parts 11 and 13 can have a considerably greater extent in the circumferential direction than the parts 10 and 12, respectively, cooperating with them. In this way, the connections 14 will be situated on the front of the diaper pants, which makes them easier to get access to for a parent who wishes to open or take off the diaper pants from an infant lying on his/her back. In the embodiment shown in FIG. 3, the parts 10 and 12 which have a small extent in the circumferential direction are advantageously made entirely of nonelastic material, for example a nonwoven.

It is of course also possible for the parts 11 and 13 to have substantially the same extent in the circumferential direction as the parts 10 and 12. In such a design, the connections 14 are situated on the user's side and are thus slightly more difficult to handle. However, such a design provides slightly better comfort for the wearer and reduces the risk of chafing.

As will be seen from FIG. 3, the unit 7 also comprises leg elastic having one or more elastic threads which can be arranged between the cover sheets 2 and 3 and are secured to these, in the stretched state, on both sides of the absorption body 1.

The liquid-permeable cover sheet 2 can be formed of, for example, a nonwoven of spunbond polypropylene. Other materials which are used for liquid-permeable cover sheets, so-called top sheets, of absorbent articles, such as nonwovens of synthetic and/or natural fibers, perforated plastic sheets or laminates of such materials, can of course also be used as cover sheet 2.

The liquid-tight outer cover sheet 3 can be a plastic sheet, preferably of the breathable type, or a laminate of a plastic sheet and a nonwoven. All materials used as so-called backing sheets for absorbent articles can be used.

The absorption body 1 preferably comprises a layer of cellulose fibers with or without admixture of superabsorbents and/or binder fibers. Other materials such as foamed material or moss can also be used. The absorption body can also be made up of several layers and advantageously comprises a layer of material with high permeability, for example a wadding.

An embodiment of a method for production of diaper pants according to FIG. 3 will now be described with reference to FIGS. 1 and 2. To simplify a comparison with the diaper pants in FIG. 3, the components in FIGS. 1 and 2 have been given the same reference numbers as corresponding components of the finished diaper pants in FIG. 3. For example, the web of liquid-permeable material in FIGS. 1 and 2 has been given the same reference number as the cover sheet 2 of the finished diaper pants.

The diaper pants according to FIG. 3 can be produced in the following way.

Absorption bodies 1 are placed on a running material web 2 of liquid-permeable material with the aid of a transfer wheel 17 on which absorption bodies 1 formed in a mat former wheel (not shown) have been deposited. If the absorption bodies 1 can be formed in synchrony with the advance of the material web 2, the transfer wheel can be omitted and the wheel 17 can be a mat former wheel. The moulds of the mat former wheel are expediently designed such that the absorption bodies leaving the mat former wheel have front ends and rear ends directed toward each other. If this is not the case, the transfer from the mat former wheel takes place in such a way that every second absorption body is turned 180° before the absorption bodies are placed on the transfer wheel 17. The absorption bodies 1 are then placed on the material web 2 in a row with front portions and rear portions of adjacent absorption bodies directed toward each other.

A material web 3 of liquid-tight material is then placed on top of the row of absorption bodies 1. The material web 3 passes a gluing unit 18 immediately before application and is secured, with the aid of a pair of rollers 19, to the material web 2 in parts lying outside the absorption bodies 1. If appropriate, the material web 3 is also secured to the rear side of each absorption body 1. Elastic threads or elastic bands 20 are inserted with the aid of a feed unit (not shown) between the webs 2 and 3 and are secured to these with the aid of the pair of rollers 19. Transverse elastic elements, waist elastic, are also expediently applied between the webs 2 and 3 before these pass through the pair of rollers 19. For the sake of clarity, this elastic is not shown in the figures, as it will be clear to the skilled person without illustration.

Figure 4:
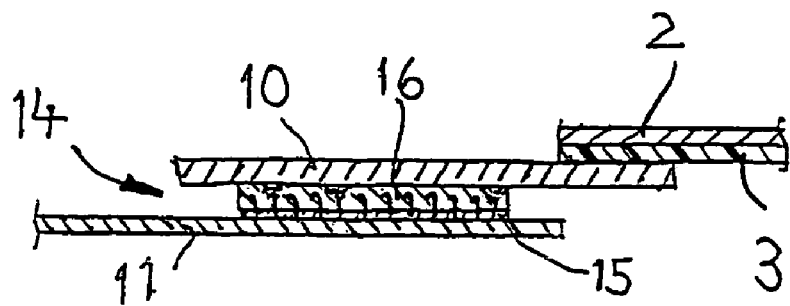
FIG. 4 shows a cross-sectional view along the line IV-IV in FIG. 3.

The combined web 1, 2, 3 of continuous diaper pants blanks then runs through a unit 21 in which side panels 8, 9 are applied to each diaper pants blank. In the embodiment shown, the side panels 8, 9 are secured to the front portions 4 of the diaper pants blanks, but they could equally well be secured to the rear portions instead. The side panels 8, 9 of two adjacent diaper pants blanks are contiguous with each other upon application and differ from the side panels shown in FIG. 3 by being rectangular. Each side panel 8, 9 has two parts 10, 11 and 12, 13, respectively, which are connected to each other by a connection 14 (not shown in FIGS. 1 and 2) which is described with reference to FIGS. 3 and 4. The unit 21 can be arranged in such a way that, on both sides of the web of continuous diaper pants blanks, it can deliver and then secure rectangular side panels 8, 9 from a store of these, or the unit can also be arranged to separate rectangular side panels from a storage roller and then deliver these and secure them to the web of continuous diaper pants blanks. The side panels are attached by adhesive bonding or welding, for example, and the unit 21 thus also comprise, in the case of adhesive bonding, a gluing unit and a stamp or the like and, in the case of welding, a welding device, for example an ultrasonic welding device.

After application of the side panels, the web of continuous diaper pants blanks runs through a cutter device 22 in which individual diaper pants blanks are cut out. In the embodiment shown, the cutter device is a blade roller which also cuts out leg openings from the diaper pants blank. In the illustrated embodiment of the diaper pants according to the invention, part of the leg openings is included in the side panels 8, 9. It is of course possible to cut out the leg openings in the web of continuous diaper pants blanks before the application of side panels, especially if the diaper pants are designed such that that part of the side panels included in the leg openings can be straight. Instead of rectangular side panels, it is of course also possible to apply side panels which have leg recesses. However, this is not preferred because it considerably increases the precision requirements for application of the side panels. The leg recesses are therefore preferably cut out after the side panels have been secured to the web of continuous diaper pants blanks. In the embodiment shown, the same blade roller is used for cutting leg openings and for dividing the web of continuous diaper pants blanks into individual diaper pants blanks, but it is of course instead possible to cut the leg openings before division by using a separate cutting device.

After the division of the web of continuous diaper pants blanks, the individual diaper pants blanks are fed to a folding device 23 via a guide arrangement (not shown), for example a guide rail and a suction conveyor. In the embodiment shown, the device 23 comprises a pair of rollers 24 and a member 25 which executes a reciprocating movement and which drives the crotch portion of the diaper pants blank into the nip of the roller pair 24 when the diaper pants blank is situated at the nip. In this way, the diaper pants blank is folded double so that the front edge is situated level with the rear edge.

To obtain finished diaper pants from the diaper pants blanks, all that is left to do is to fold the side panels in across the rear portion of the diaper pants blanks and secure the side panels to these. It is simplest to secure the side panels to the rear portion by gluing. Every second double-folded diaper pants blank leaving the folding device 23 will have the front portion uppermost, and every other one will have the rear portion uppermost. This means that for every second double-folded diaper pants blank, the glue will be applied from above along the edges of the free ends of the side panels, and for every other diaper pants blank the glue will be applied from below. For this purpose, two gluing sprays 25, 26 are arranged for alternate use. Likewise, every second pair of side panels 8, 9 are folded upward and every other pair downward, and two devices 27, 28 are provided to alternately fold the side panels in across the rear portions and secure them to these. The devices 27, 28 can each comprise a pivot arm or the like which, with the aid of a vacuum, takes hold of the free ends of the side panels on their unglued side and then folds the side panels in across the rear portions and presses the glued side of the free ends of the side panels against the side areas of the rear portions. The devices 27, 28 also comprise a movable counterstay against which the pivot arms press. The diaper pants blanks are expediently fed intermittently past the gluing sprays 25, 26 and the devices 27, 28 and leave the devices 27, 28 as finished diaper pants.

The web 3 of liquid-tight material can be placed on top of the web 2 of liquid-permeable material after the absorption bodies have been placed thereon. It is of course possible to switch the webs around so that absorption bodies are placed on the web of liquid-tight material, and the web of liquid-permeable material is applied last.

By virtue of the fact that the detachable and resealably connected two-part side panels are applied to the web of continuous diaper pants blanks in the sealed state, the precision requirements when arranging the side panels on the web of continuous diaper pants blanks are reduced compared to the situation if the parts of the side panels were each to be applied individually, because a deviation from the desired position of the side panels, for example in the longitudinal direction, does not entail an offset of the mutual positions of the parts included in the resealable connection. In the event of such a deviation of a side panel whose free end contains a male element which is intended to interact with a female element secured to the outer cover of the diaper pants, the male and female elements of the securing arrangement will be offset in relation to each other. This means that the resistance to opening of the connection is less than intended, the diaper pants have a less attractive appearance, and the fit after opening and resealing is not as good as intended, if one assumes that the male and female elements after opening are joined together so that they completely overlap each other.

The arrangement of the diaper pants blanks so that the front and rear portions of adjacent diaper pants blanks are directed toward each other also means that two side panels can be arranged in one piece and then divided by a straight cut in connection with the cutting of individual diaper pants blanks. This can ensure that the waist edges of the side panels and the part of the diaper pants containing the absorption body are always at the same level, which can be difficult to achieve upon application of individual side panels. It should be noted that, in a web of continuous diaper pants blanks in which the front portions are directed in the same sense so that the front portion of one diaper pants blank is directed toward the rear portion of the nearest leading diaper pants blank, very great precision is needed when dividing the web into individual diaper pants blanks by means of straight cuts, so as to ensure that part of the rear portion does not end up in the front portion, or part of the front portion end up in the rear portion. If the front and rear portions have the same width and the same material composition, this has no great effect, but, if these portions have a different width or different material composition, it is important to ensure that the cut is made in exactly the right place. By means of the methods described as embodiments of the invention herein, the tolerances for the positioning of the side panels are thereby increased, and at the same time the position of the dividing cuts requires less precision compared to methods in which a separate side panel for each front portion is applied.

In addition, the childproof connection can be made with great care and precision since this is done in a production step before the actual diaper production. It is thus possible to use optimum web speeds, which can be considerably slower than the web speeds normally pertaining in process lines for diaper production. A number of parallel side panel blanks can be produced simultaneously if the web width is great enough. In this way, a large number of side panels can be prefabricated per unit of time without the web speed being too high.

The described method can of course be modified within the scope of the invention. For example, the side panels 8, 9 can be applied to the material web 2 before the material web 3 is applied, so that the side panels are arranged between the material webs 2 and 3 and are secured to both of these webs. The side panels can also be secured to the liquid-permeable cover sheet. The absorption bodies 1 can be completed with further layers, such layers being applied on top of the bodies 1 by means of further transfer or mat former wheels being added to the arrangement shown in FIGS. 1 and 2. Moreover, members for providing liquid barriers, so-called standing gathers, can be added to the arrangement. The waist elastic, which preferably extends along the front edge and rear edge of the diaper pants, does not need to be arranged between the material webs 2 and 3 and can instead be applied upon one of these webs. The absorption bodies can have a shape other than that shown, for example they can be rectangular or hourglass-shaped. Types of securing elements other than VELCRO™ members can be used, for example different types of snap-fit connections, which can also be made childproof. It is also conceivable for the side panels to be made up of two parts with the same dimension in the circumferential direction. The components included in the arrangement described are of a type generally used in production of diapers, diaper pants and similar articles and can be replaced by other components with the same function, for example the blade roller can be replaced with a punch device. The invention is therefore limited only by the content of the attached patent claims.

Although only preferred embodiments are specifically illustrated and described herein, it will be appreciated that many modifications and variations of the present invention are possible in light of the above teachings and within the purview of the appended claims without departing from the spirit and intended scope of the invention.

What is claimed is:

1. A method for production of disposable diaper pants or of a sanitary panty of the disposable type with openable and resealable side panels, the method comprising:

forming a web of interconnected diaper pants blanks, each diaper pants blank having an absorption body enclosed between an inner cover sheet of liquid-permeable material and an outer cover sheet of liquid-impermeable material and having a front portion and a rear portion and an intermediate crotch portion, by applying a row of absorption bodies being applied on a continuous web of inner or outer cover sheet material so that the front portions and the rear portions of adjacent diaper pants blanks in the web of interconnected diaper pants blanks are directed toward each other, thereafter applying a continuous web of outer or inner cover sheet material to the web with absorption bodies and secured to it in those parts thereof which lie outside the absorption bodies;

securing separate side panels connected to each other to the side portions of each of the adjacent front portions or each of the adjacent rear portions of the diaper pants blanks, each side panel comprising two parts which are connected to each other by means of a detachable and resealable connection;

cutting out individual diaper pants blanks having side panels from the web of interconnected diaper pants blanks;

folding each diaper pants blank about a transverse axis in the crotch portion so that the front and rear edges of the blank lie against each other; and thereafter folding the side panels of each diaper pants blank in toward those side portions of either the rear portion or front portion which have no side panel and are secured thereto.

2. The method according to claim 1, wherein the side panels are secured to the outer or inner cover sheet of the diaper pants blanks.

3. The method according to claim 1, wherein the side panels are placed between the outer and inner cover sheets of the web of connected diaper pants blanks and are secured to both of these sheets.

4. The method according to claim 1, wherein the side panels at least partially comprise an elastic material.

5. The method according to claim 1, wherein the detachable and resealable connection, which connects the two parts of each side panel to each other, is a childproof connection.

6. The method according to claim 1, wherein in addition to the detachable and resealable connection, each side panel also comprises a second childproof connection which is detachable and which is destroyed when the side panel is opened for the first time.

* * * * *